(12) United States Patent
Iketani (10) Patent No.: US 7,248,296 B2
(45) Date of Patent: Jul. 24, 2007

(54) AUTOMATIC GAIN CONTROL DEVICE FOR ELECTRONIC ENDOSCOPE

(75) Inventor: Kohei Iketani, Saitama (JP)

(73) Assignee: PENTAX Corporation, Tokyo (JP)

(*) Notice: Subject to any disclaimer, the term of this patent is extended or adjusted under 35 U.S.C. 154(b) by 810 days.

(21) Appl. No.: 10/446,849

(22) Filed: May 29, 2003

(65) Prior Publication Data

US 2003/0222997 A1   Dec. 4, 2003

(30) Foreign Application Priority Data

May 31, 2002   (JP)   ............................. P2002-158462

(51) Int. Cl.
*H04N 5/235*   (2006.01)
(52) U.S. Cl. ..................... 348/255; 348/229.1; 348/241
(58) Field of Classification Search .................. 348/45, 348/223.1, 222.1, 255.1, 229.1, 230.1, 255; 600/101; 358/522; 396/17
See application file for complete search history.

(56) References Cited

U.S. PATENT DOCUMENTS

| | | | | |
|---|---|---|---|---|
| 5,016,093 A | * | 5/1991 | Yoshida ..................... 348/224.1 |
| 5,485,203 A | * | 1/1996 | Nakamura et al. ............ 348/263 |
| 5,982,424 A | * | 11/1999 | Simerly et al. ............ 348/229.1 |
| 6,080,104 A | | 6/2000 | Ozawa et al. |
| 6,130,724 A | * | 10/2000 | Hwang ......................... 348/678 |
| 6,163,342 A | * | 12/2000 | Suzuki ......................... 348/364 |
| 6,638,212 B1 | * | 10/2003 | Oshima ........................ 600/109 |
| 6,669,628 B2 | * | 12/2003 | Abe ............................. 600/118 |
| 6,747,694 B1 | * | 6/2004 | Nishikawa et al. ........ 348/229.1 |
| 6,750,906 B1 | * | 6/2004 | Itani et al. ................ 348/229.1 |
| 6,993,183 B2 | * | 1/2006 | Inoue ........................... 382/170 |
| 7,081,921 B2 | * | 7/2006 | Nitta et al. ............... 348/229.1 |
| 7,098,946 B1 | * | 8/2006 | Koseki et al. ............ 348/229.1 |
| 7,102,669 B2 | * | 9/2006 | Skow ......................... 348/222.1 |
| 2002/0176009 A1 | * | 11/2002 | Johnson et al. ............. 348/229 |

* cited by examiner

*Primary Examiner*—David Ometz
*Assistant Examiner*—Pritham D. Prabhakher
(74) *Attorney, Agent, or Firm*—Greenblum & Bernstein, P.L.C.

(57) ABSTRACT

An automatic gain control device for an electronic endoscope is provided and comprises a controllable gain amplifier, an A/D converter, a histogram circuit, and a CPU. The controllable gain amplifier amplifies image signals from an imaging device. Amplified image signals from the controllable gain amplifier are input to the A/D converter. A histogram of the amplified image signals from the controllable gain amplifier is produced by the histogram circuit when an image taken in a white-balance test accessory is taken. By using the CPU, the gain of the controllable gain amplifier is adjusted in accordance with the determination of whether a saturated pixel exists for signals in the tolerance range of the A/D converter, so that a linear region of the image signals from the controllable gain amplifier substantially coincides with the tolerance range.

17 Claims, 6 Drawing Sheets

FIG. 9

AUTOMATIC GAIN CONTROL DEVICE FOR ELECTRONIC ENDOSCOPE

BACKGROUND OF THE INVENTION

1. Field of the Invention

The present invention relates to an electronic endoscope apparatus that is used for observing an internal organ in a human body, an object inside a duct, and the like.

2. Description of the Related Art

An electronic endoscope apparatus generally comprises an electronic endoscope with a flexible conduit (or insertion portion) which is inserted into a body or a duct, an image-signal processing device that processes image signals from a CCD which is provided at the distal end of the flexible conduit, and an image-indicating device (or a TV monitor) for monitoring images captured by the CCD. Electronic endoscopes are detachable from the image-signal processing device so that a suitable electronic endoscope can be attached to the image-signal processing device as required. When an electronic endoscope is attached to the image-signal processing device, image signals from the electronic endoscope are amplified and are subjected to A/D conversion, and other types of signal processing are carried out.

The relationship between a received light amount on a CCD and intensity of the signal (voltage) output from the CCD has a linear region and a nonlinear saturated region. A threshold voltage that determines the boundary of the linear region and the saturated region is defined as a saturation voltage. The gain of an amplifier provided in the image-signal processing device for processing image-signals from the electronic endoscope is preferably preset to the level that excludes the saturation level of the amplified image-signals from the tolerance range of the A/D converter. However, since the saturation voltage for the same type of CCD, manufactured in the same lot, is uneven, a suitable gain for the image signals in the image-signal processing device is different for each of the electronic endoscopes attached to the image-signal processing device. Conventionally, the gain of an image-signal processing device is adjusted to a level that covers a CCD with the minimum saturation voltage level, so that an insufficient signal output does not occur for any electronic endoscope.

However, when the gain of an image-signal processing device is preset to the value that covers the minimum saturation voltage for all of the CCDs, image signals from an electronic endoscope with a high output voltage are superfluously amplified by the preset gain and this makes the S/N ratio worse. Namely, reproduced images deteriorate because of noise even though the image signals are obtained at a sufficiently high level and the ability of the CCD to produce quality images is not fully utilized.

SUMMARY OF THE INVENTION

Therefore, an object of the present invention is to provide an automatic gain control device that is able to amplify image signals to a proper gain that is based on the saturation voltage characteristics of an imaging device, and further, to provide an electronic endoscope apparatus in which the automatic gain control device is provided.

According to the present invention, an automatic gain control device for an electronic endoscope is provided that comprises a controllable gain amplifier, an A/D converter, a histogram generating processor, a saturated pixel detecting processor, and a gain control processor.

The controllable gain amplifier, of which the gain is controllable, amplifies image signals from an imaging device. The A/D converter digitalizes the analog amplified image signals from the controllable gain amplifier. The histogram generating processor produces a histogram based on reference image signals amplified by the controllable gain amplifier when the image signals represent an image taken in a white-balance test accessory. The saturated pixel detecting processor determines whether a photodiode that has reached its saturation voltage level, exists for signals in a tolerance range of the A/D converter. The gain control processor adjusts the gain in accordance with the determination of the saturated pixel detecting processor so that a linear region of the image signals from the controllable gain amplifier substantially coincides with the tolerance range of the A/D converter.

Further, according to the present invention, an automatic gain control device for an electronic endoscope is provided that comprises a controllable gain amplifier, an image-signal processing circuit, a histogram generating processor, a saturated pixel detecting processor, and a gain control processor.

The controllable gain amplifier, of which the gain is controllable, amplifies image signals from an imaging device. The image-signal processing circuit carries out certain kinds of signal processing on the amplified image signals from the controllable gain amplifier. The histogram generating processor produces a histogram based on reference image signals amplified by the controllable gain amplifier when the reference image signals represent an image taken in a white-balance test accessory. The saturated pixel detecting processor determines whether a pixel that has reached a saturation voltage level, exists for signals in a tolerance range of the A/D converter. The gain control processor adjusts the gain in accordance with the determination of the saturated pixel detecting processor so that a linear region of the image signals from the controllable gain amplifier substantially coincides with the tolerance range of the image-signal processing circuit.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention is described below with reference to the embodiments shown in the drawings.

Figure 1:
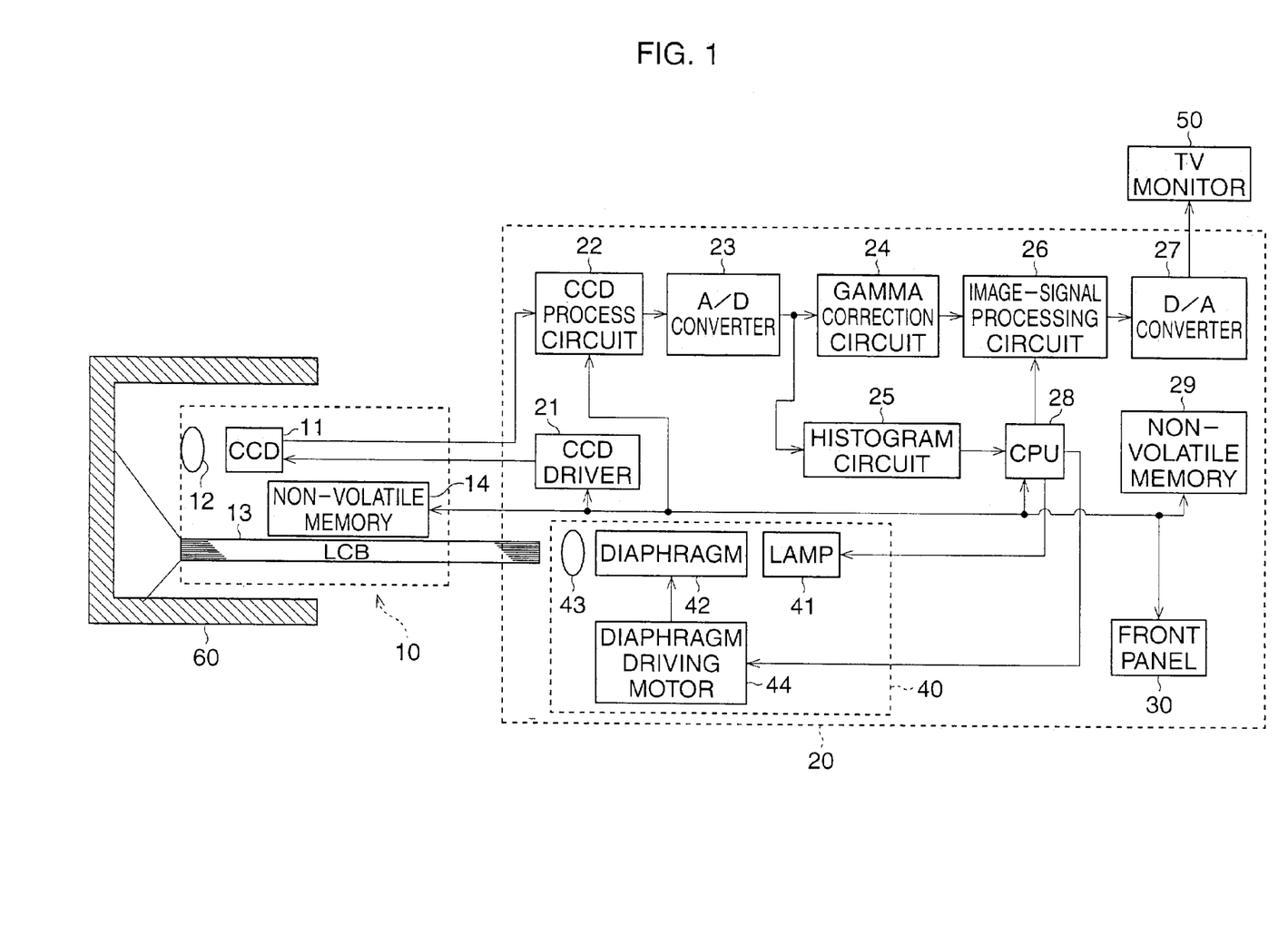
FIG. 1 is a block diagram of an electronic endoscope system of the first embodiment of the present invention.

FIG. 1 is a block diagram of an electronic endoscope system of the first embodiment of the present invention. The electronic endoscope apparatus of the present embodiment generally comprise an electronic endoscope 10, an image-processing device 20, and a TV monitor 50. The electronic endoscope 10 is detachably connected to an image-signal processing device 20, and the TV monitor 50 is connected to a video output terminal of the image-signal processing device 20 through a video signal cable. Although in the present embodiment, only the TV monitor 50 is shown as an example of a peripheral device, a video printer, VCR, or computer may also be connected to the image-signal processing device 20.

The electronic endoscope 10 has an insertion portion that is formed with a flexible conduit. An imaging device, such as a CCD 11, is provided at the distal end of the conduit, so that an image of an internal body or a tube is captured by the CCD 11 through an objective lens 12. Inside the electronic endoscope 10, a light guide cable (LCB) 13, which is comprised of a superfine optical fiber bundle, is provided to transmit illumination light for image-pickup operations of the CCD 11. Further, a memory 14 is provided inside the electronic endoscope 10. Note that, the memory 14 is a non-volatile memory and may store a model name or a serial number of the electronic endoscope to distinguish each electronic endoscope from the others.

The electronic endoscope 10 is attached to the image-signal processing device 20 via a connector (not shown). Thereby, the light guide cable 13 is optically connected to a light source portion 40 that is provided inside the image-signal processing device 20. The light source portion 40 comprises a lamp 41, a diaphragm 42, a condensing lens 43, a diaphragm driving motor 44, and so on. Light emitted from the lamp 41 is made incident to an end face of the light guide cable 13 through the diaphragm 42 and through the condensing lens 43. The diaphragm 42 is a device for adjusting the light amount supplied to the light guide cable 13 from the lamp 41 and it is operated by the driving motor 44. The lamp 41 and the diaphragm driving motor 44 are controlled by a CPU 28. Further, when a sequential imaging system is needed for the electronic endoscope system, a rotational RGB color filter may also be provided in the light path with the diaphragm.

The CCD 11 is electrically connected to a CCD driver 21 and a CCD process circuit 22 inside the image-signal processing device 20. Namely, the CCD 11 is controlled by drive signals from the CCD driver 21 and captures images at the distal end of the insertion portion, which is illuminated by light transmitted from the light source portion 40 via the light guide cable 13. Images captured by the CCD 11 are converted to analog image signals and fed to the CCD process circuit 22. The analog image signals are then amplified at a predetermined gain and subjected to a blanking process, clamp process, color separation process (e.g. separation to luminance signals and color difference signals by a matrix circuit), and the like, which are well known in the art, and finally output to an A/D converter 23. The image signals are converted to digital signals at the A/D converter 23 and are then output to a gamma correction circuit 24 and a histogram circuit 25. From the gamma correction circuit 24 the image signals are output to an image-signal processing circuit 26 after carrying out a gamma correction process. In the image-signal processing circuit 26, typical image-signal processing processes known in the art, such as a white balance correction process and so on, are executed. The image signals are then subjected to a decoding process and output to a D/A converter 27. Finally, the image signals are converted to analog video signals of the NTSC standard, PAL standard, or the like, and then fed to the TV monitor 50. Note that the white balance correction process at the image-signal processing circuit 26 is controlled by the CPU 28.

At the histogram circuit 25, the histogram for the luminance signals (Y) or reference image signals is obtained and the histogram data is output to the CPU 28. Namely, frequencies (the number or pixels) for each interval of the digital luminance signal (Y) values within the tolerance range of the A/D converter 23 are detected for each image or each set of images. The CPU 28 controls the gain of the CCD process circuit 22 in accordance with the histogram of the luminance signals (Y).

The CCD driver 21, a non-volatile memory 29, and the memory 14 inside the electronic endoscope are also connected to the CPU 28 and controlled by control signals from the CPU 28. Further, a front panel 30 with various kinds of switches and an indicator, is connected to the CPU 28, so that the CPU 28 cooperatively controls each circuit in accordance with the operation of the switches.

With reference to FIG. 2 to FIG. 5, the relation between the output of the CCD 11 and the gain of the CCD process circuit 22 is explained in the following.

Figure 2:
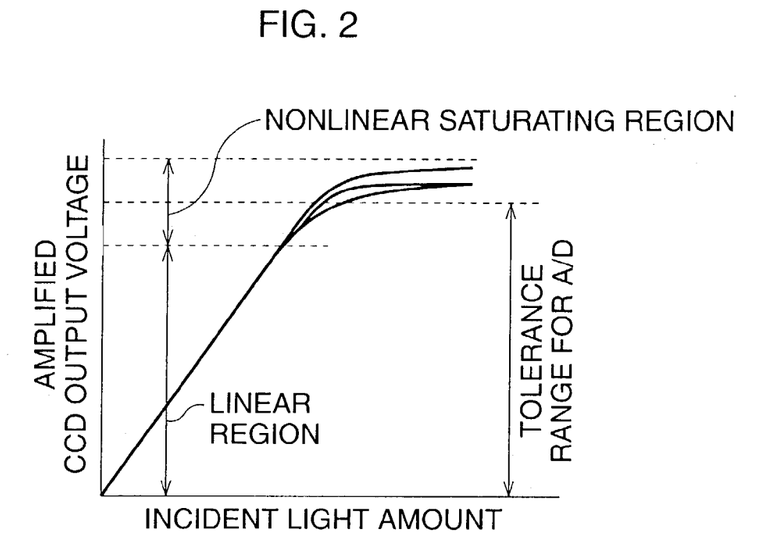
FIG. 2 shows relations between the amount of light made incident to the CCD and voltage values input to an A/D converter when the gain of a CCD process circuit is insufficient for the output of the CCD.
Figure 3:
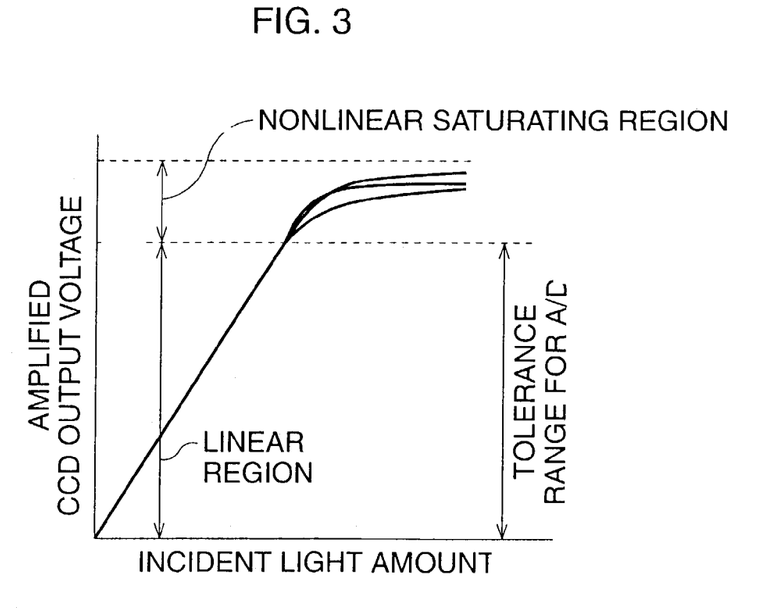
FIG. 3 shows relations between the amount of light made incident to the CCD and voltage values input to an A/D converter when the gain is properly adjusted.
Figure 4:
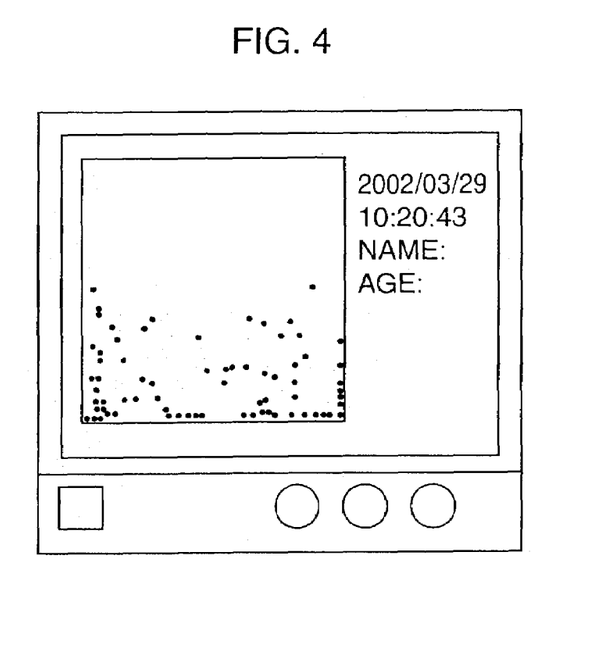
FIG. 4 schematically illustrates an example of output on the monitor screen under the same conditions as those of FIG. 2.
Figure 5:
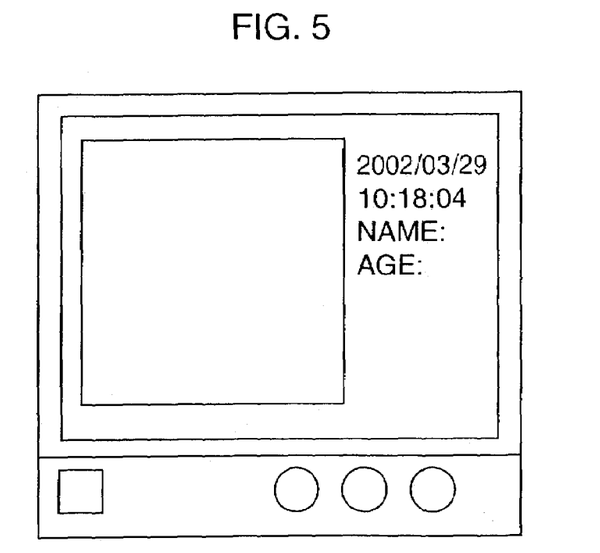
FIG. 5 schematically illustrates an example of output on the monitor screen under the same conditions as those of FIG. 3.

FIG. 2 and FIG. 3 are graphs showing the relation between the amount of light made incident to the CCD 11 and the voltage values input to the A/D converter 23. The amount of light made incident to the CCD 11 is indicated by the abscissa and the voltage values are indicated by the ordinate. FIG. 2 illustrates the situation when the gain of the CCD process circuit 22 is insufficient for the output of the CCD 11, and FIG. 3 illustrates the situation when the gain is properly adjusted. On the other hand, FIG. 4 and FIG. 5 schematically illustrate examples of output on the monitor screen for the situation in FIG. 2 and FIG. 3, respectively.

The output signal of the CCD 11 proportionally increases as the amount of incident light increases until the amount of incident light exceeds the saturation voltage of the photodiodes of the CCD 11. When it reaches the saturated region, the increase rate of the output voltage from the CCD 11 declines as the amount of incident light increases. Therefore, the output voltage of the amplified image signals levels off in the saturated region, as shown in FIG. 2 and FIG. 3. The saturation voltages for each of the photodiodes in the single CCD are different from one another and are not uniform. Therefore, when the gain is preset to an insufficient level, i.e. when the saturated regions of some of the photodiodes are within the tolerance range of the A/D converter 23 as shown in FIG. 2, these photodiodes (pixels or light receiving elements of an imaging device) reach the saturation level when the output levels of the CCD 11 are high, and appear as dark spots on the monitor screen, as shown in FIG. 4. On the other hand, when the gain is preset to a sufficient level, i.e. when the linear region of the amplified image signals for all pixels is adjusted to the tolerance range of the A/D converter 23, as shown in FIG. 3, a dark spot never appears on the monitor screen even when the output levels of the photodiodes of the CCD 11 are high.

Figure 6:
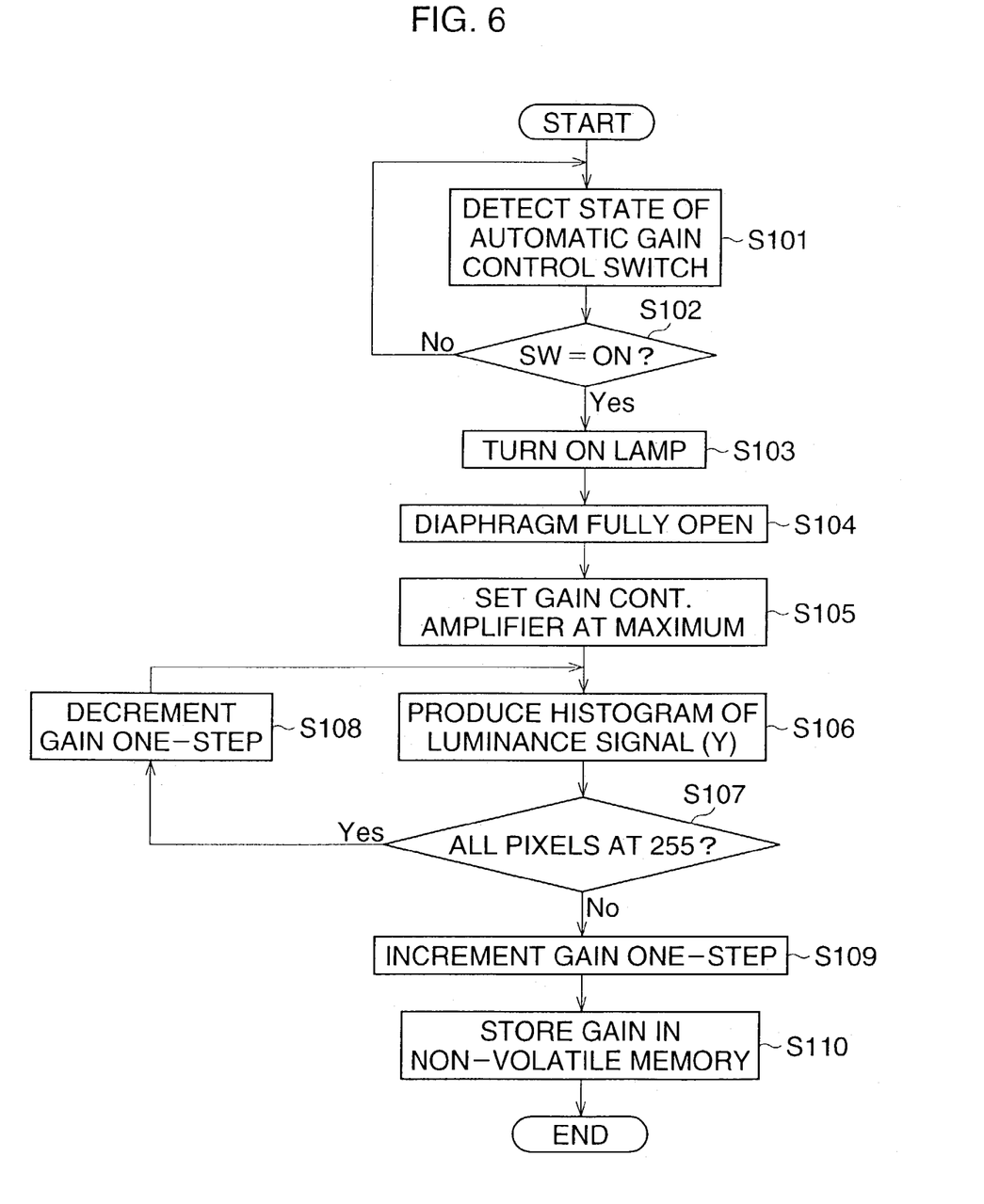
FIG. 6 is a flow chart of an automatic gain control operation of the first embodiment.

With reference to FIG. 1 and FIG. 6, an automatic gain control operation carried out by the CPU 28 in the first embodiment will be explained. FIG. 6 is a flow chart of the automatic gain control operation of the first embodiment. The operation is carried out with the end of the electronic endoscope 10 inserted into a white-balance test accessory 60. The white-balance test accessory 60 is a cup-like device with its inside coated with white paint. It is used for correcting or adjusting the white balance of the electronic endoscope system.

In Step S101, a signal that represents a state (SW) of an automatic gain control switch, which may be provided on the front panel 30, is input to the CPU 28. In Step S102, it is determined whether the state of the automatic gain control switch is the ON state. When the state is not the ON state, the process returns to Step S101 and the above processes are repeated. Note that, Steps S101 and S102 may be carried out as an interrupt routine in the system operation.

On the other hand, when it is determined in Step S102 that the state (SW) of the automatic gain control switch is the ON state, then the lamp 41 is turned ON in Step S103 and the diaphragm 42 is fully opened in Step S104. Further, in Step S105, the gain of a controllable gain amplifier provided inside the CCD process circuit 22 is then set to the maximum value. Namely, at the beginning of the operation, images of the bottom surface of the white-balance test accessory 60 are captured by the CCD 11 with the diaphragm fully open and with the maximum gain. Note that, the gain of the controllable gain amplifier inside the CCD process circuit 22 can be controlled by the CPU 28 by step-by-step increments or decrements.

In Step S106, the CPU 28 controls the histogram circuit 25 so that the luminance signals (Y), which are output from the CCD 11 and amplified by the controllable gain amplifier of the CCD process circuit 22, are observed and their histogram is obtained. According to the histogram data, whether the output values of the luminance signals (Y) for all pixels in the CCD 11 are at a maximum value is determined in Step S107. For example, when the A/D converter 23 converts the luminance signals to eight-bit data, i.e. when the maximum value of the luminance signals is 255, whether the luminance signal (Y) value for all pixels is 255, is determined. When the intensity of the luminance signals (Y) from each of the pixels are all at the maximum value (255), the gain of the controllable gain amplifier is decremented one-step in Step S108, and the process returns to Step S106. Namely, steps S106-S108 are repeated until at least one pixel of which the luminance signal (Y) is less than the maximum value (255) appears.

When it is determined, in Step S107, that there exists a pixel with less luminance signal (Y) than the maximum value, among all the pixels of the CCD 11, the gain of the controllable gain amplifier is incremented one-step in Step S109. Thereby, the linear regions of the amplified image signals, which correspond to each pixel, are substantially adjusted to the tolerance range of the A/D converter 23. In Step S110, the value of the gain, which is adjusted in Step S109, is stored in the memory 29 together with the model name or the serial number of the electronic endoscope 10. At the same time, the gain value is also stored in the memory 14 inside the electronic endoscope 10, and the automatic gain control operation of the first embodiment ends.

The above automatic gain control operation can be carried out in the white balance correction process. Therefore, with reference to FIG. 6 and FIG. 7, an alternate embodiment of the first embodiment, in which the automatic gain control operation is carried out in combination with the white balance correction process, will be explained.

Figure 7:
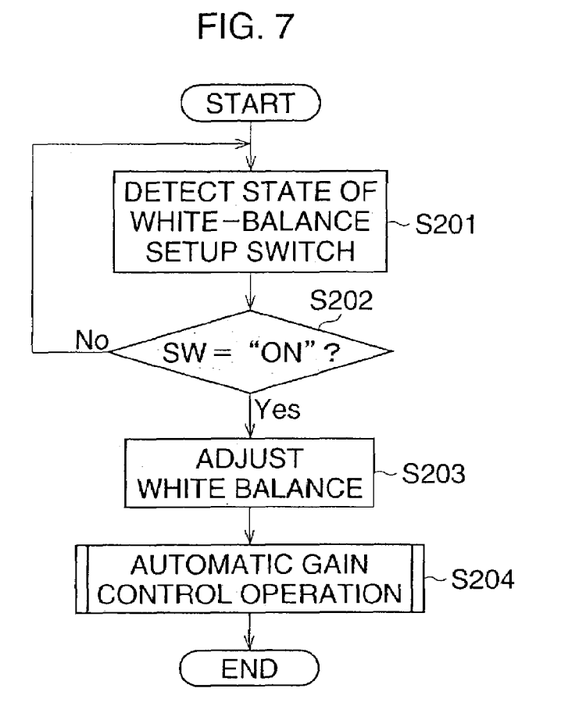
FIG. 7 is a flow chart of an alternate embodiment of the first embodiment that comprises the automatic gain control operation in FIG. 6.

As it is similar to the automatic gain control operation described in FIG. 6, the present white-balance and automatic gain control operations are also carried out with the distal end of the electronic endoscope 10 kept inside the white-balance test accessory 60. In Step S201, the state (SW) of a white-balance setup switch, on the front panel 30, is detected by the CPU 28. Further, whether the state (SW) of the white-balance setup switch is the ON state is determined in Step S202. When the state (SW) is not the ON state, the process returns to Step S201 and the same processes are repeated. When the state (SW) of the white-balance setup switch is determined as the ON state, in Step S202, the process proceeds to Step S203. Note that, Steps S201 and S202 may be carried out as an interrupt routine in the system operation.

In Step S203, the white balance correction process is carried out. Namely, the lamp 41 is turned ON, the diaphragm 42 is opened to a predetermined aperture, and the relative gain values for each R and B signals are adjusted to G signal at the image-signal processing device of FIG. 1, in accordance with the operation of the switches provided on the front panel 30. When the white balance correction process completes, the automatic gain control operation is then carried out in Step S204. Namely, the operations in Step 104 to Step 110 described in FIG. 6 are executed in Step S204.

Figure 8:
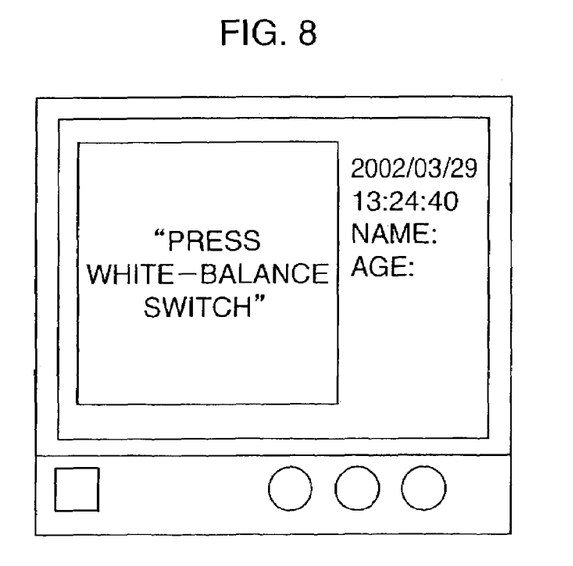
FIG. 8 schematically illustrates an example of output on the monitor screen when the gain is not stored in the memories in advance.

Note that, whether the gain value data is stored in the memory 14 or 29 may be determined before the above white-balance and automatic gain control operations are started, so that when the gain is not stored in the memories 14 and 29 in advance, a message that prompts the execution of the white-balance and automatic gain control operations, e.g. "Press White-Balance Switch", may be indicated on the TV monitor 50, as shown in FIG. 8. Further, when the automatic gain control operation has already been carried out and the proper gain for the electronic endoscope, which is attached to the image-signal processing device, is stored in the memory 14 or 29, the gain of the controllable gain amplifier provided inside the CCD process circuit 22 is set to the value stored in the memory 14 or 29.

As described above, according to the first embodiment of the present invention, the gain of the image signals in the image-signal processing device can be automatically adjusted in accordance with the saturation voltage of the imaging device (in detail the saturation voltage of each photodiode in the imaging device) mounted inside the individual electronic endoscopes. Namely, the gain for a certain electronic endoscope (or imaging device) can be automatically adjusted to a value that is adopted for the photodiode having the minimum saturation voltage in the imaging device. Therefore, for each individual electronic endoscope, the gain is automatically set to the minimum value which is sufficient for the linear region of all amplified image signals from the imaging device, to be adjusted to the tolerance range of the A/D converter. Thereby, the S/N ratio of the image signals is maximized for all electronic endoscopes that are used in the system and a high-quality image with reduced noise is obtained. As a result, a serious spot relating to a disease can be easily detected and confirmed in the endoscopy. Further, according to the present embodiment, the gain is automatically adjusted while executing the white balance correction, so that an operator can easily carry out the adjustment without any cumbersome operations.

Figure 9:
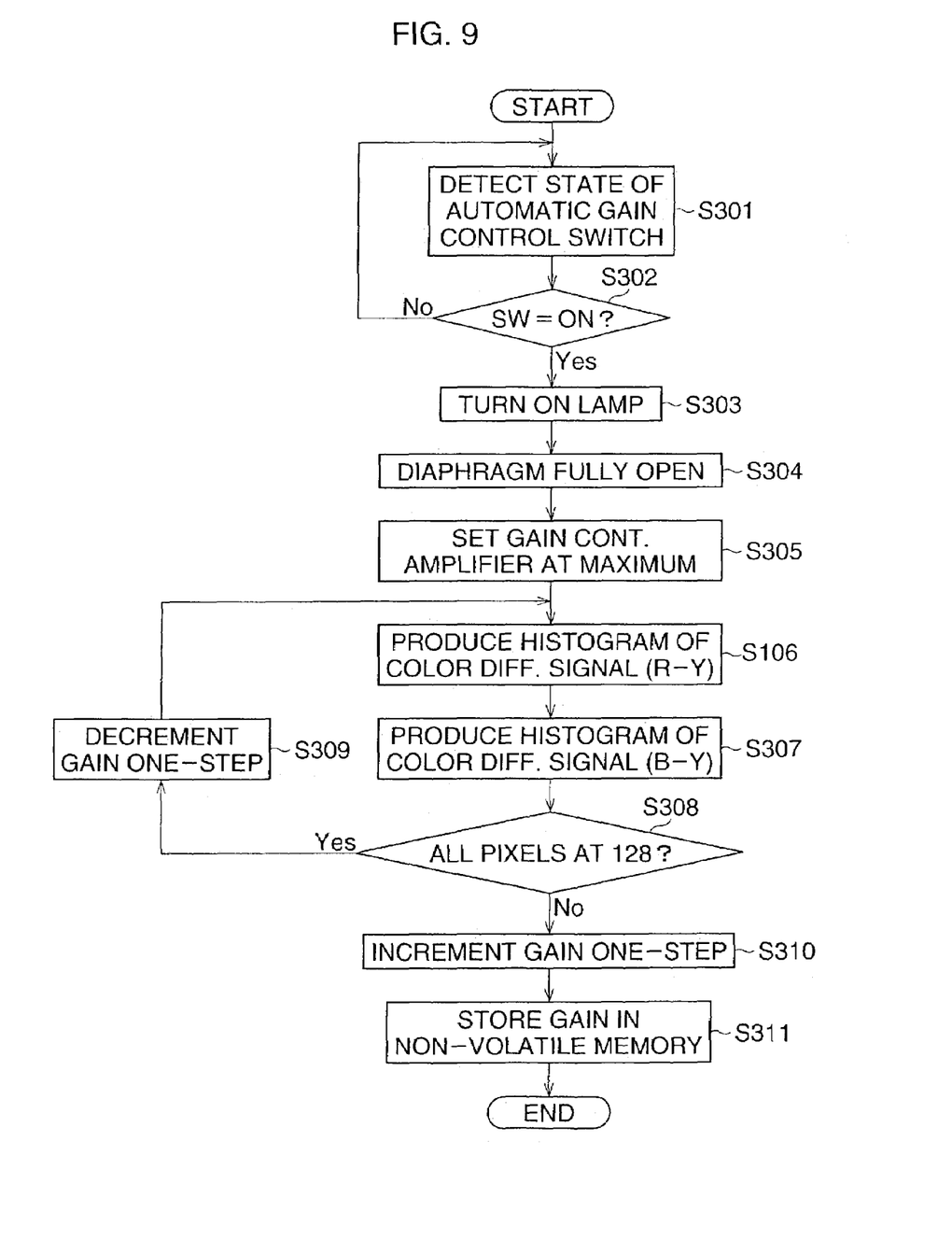
FIG. 9 is a flow chart of an automatic gain control operation of the second embodiment.

With reference to FIG. 9, the second embodiment of the present invention will be explained. In the first embodiment, the gain control or adjustment is based on the luminance signal (Y), however, in the second embodiment, the gain is controlled with respect to the color difference signals (R-Y, B-Y). Note that, the other structures in the second embodiment are similar to those in the first embodiment, so that explanations are omitted for structures similar to those of the first embodiment.

In Step S301, the state (SW) of the automatic gain control switch on the front panel 30 is detected by the CPU 28. In Step S302, whether the state (SW) of the automatic gain control switch is the ON state is determined. When it is not the ON state, the process returns to Step S301 and the above processes are repeated.

When it is determined, in Step S302, that the state (SW) is the ON state, the lamp 41 is then turned ON in Step S303 and the diaphragm 42 is fully opened in Step S304. In Step S305, the gain of the controllable gain amplifier provided inside the CCD process circuit 22 is then set to the maximum level. Namely, an image of the bottom surface of the white-balance test accessory 60 is captured by the CCD 11 with the diaphragm 42 fully opened and the gain at the maximum.

In Step S306, the color difference signals (R-Y), which are output from the CCD 11 and amplified by the controllable gain amplifier of the CCD process circuit 22, are observed and their histogram is obtained. Further, in Step S307, the color difference signals (B-Y), which are output from the CCD 11 and amplified by the controllable gain amplifier-of the CCD process circuit 22, are observed and their histogram is obtained. In Step S308, whether the color difference signals (R-Y) and the color difference signals (B-Y) for all of the pixels are at the median is determined (here, "pixel" means a picture element for the output device, such as a TV monitor and the like, of which the color is comprised of signals from a plurality of pixels in the CCD). For example, when the color difference signals are converted to eight-bit data, of which the maximum value is 255, whether the intensities or values of the color difference signals for all of the pixels are 128 is determined (here, "128" being half the maximum value "255" represents the achromatic position as described below).

The values of the color difference signals (R-Y, B-Y) coincide with the median being half the maximum value only when they represent white color. In other words, when the values are bigger or smaller than the median, the detected color is nonwhite. Further, when the values of the color difference signals (R-Y, B-Y) are apart from the median, the nonwhite color is deepened.

An erroneous gain may be set in the first embodiment, which uses the luminance signals (Y), when the insertion portion of the electronic endoscope 10 is improperly inserted into the white-balance test accessory 60, so that a part of a black colored supporting member that supports the distal end of the insertion portion is imaged by the imaging device, or when there exists a taint, such as a black or gray spot, inside the white-balance test accessory, since the luminance signals (Y) for some of the pixels that have not reached the saturation level do not output the maximum luminance signals (Y) On the other hand, for the color difference signals (R-Y, B-Y), the output levels of the signals coincide with the median 128 to the maximum value 255 when an observed image is white, regardless of its gradation. However, the saturation voltage values for each of the photodiodes in the CCD 11 are unequal, so that the color of a pixel (a picture element for the output device), comprising a photodiode under the saturation level, leans toward a certain nonwhite color and one of the color difference signals (R-Y) or (B-Y) shifts from the median (128). Therefore, by detecting this shift, the saturation voltage for all of the photodiodes in the CCD 11 can be monitored.

When it is determined in Step S308 that the color difference signals (R-Y) and (B-Y) for all pixels are at the median (128), the gain of the controllable gain amplifier is decremented by one-step in Step S309 and then the process returns to Step S306. Namely, the processes in Steps S306 through S309 are repeated until at least one pixel of which the color difference signal (R-Y) or color difference signal (B-Y) is not at the median (128) appears.

When it is determined in Step S308 that a pixel with its color difference signal (R-Y) or (B-Y) not equal to the median, exists among the pixels, the gain of the controllable gain amplifier is incremented by one-step in Step S310. Thereby, the linear regions of all the amplified image signals are suitably adjusted to the tolerance range of the A/D converter 23. In Step S311, the value of the gain adjusted in Step S310 is stored in the memory 29 with the model name or the serial number of the electronic endoscope 10, and at the same time, the value of the gain is also stored in the memory 14 of the electronic endoscope 10. Accordingly, the automatic gain control operation program for the second embodiment ends.

As described above, according to the second embodiment, the same effect as that in the first embodiment can be achieved. Further, in the second embodiment, as an alternative to the luminance signals of the first embodiment, the color difference signals are used for monitoring the saturation voltage of the imaging device to adjust the gain, so that the gain can be properly adjusted even when the electronic endoscope is improperly inserted in the white-balance test accessory or when the surface inside the white-balance test accessory is tainted.

Note that, in the present embodiment, the image signals from an electronic endoscope, which are amplified by the controllable gain amplifier, are input to the A/D converter; however, a signal processor may be directly and subsequently connected to the controllable gain amplifier. In this construction, the gain of the controllable gain amplifier is adjusted to the tolerance range of the signal processor, so that the saturated region of the amplified image signals do not enter the tolerance range. Although in the present embodiment, the white balance correction is carried out in the image-signal processing circuit, which is subsequent to the CCD process circuit, the white balance correction may be carried out in the CCD process circuit and further it may be carried out prior to the amplification by the controllable gain amplifier.

In the present embodiment, a simultaneous imaging system, which uses an imaging device with an on-chip color filter to capture each color component image simultaneously, is adopted for the electronic endoscope system, however, a sequential imaging system can also be adopted in the system. In the sequential imaging system, R, G, and B image signals from the CCD are amplified by the controllable gain amplifier provided inside the image-signal processing device and converted to digital signals by an A/D converter. Further the R, G, and B image signals are temporally stored in the image memory in turn. When one set of R, G, and B image signals is prepared in the image memory, these R, G, and B image signals are simultaneously fed to a matrix circuit and converted to luminance and color difference signals. The luminance or color difference signals are then output to the histogram circuit so as to obtain the histogram of the luminance or the color difference signals.

Thereby, the gain of the controllable gain amplifier is adjusted in accordance with the embodiments described above.

Although in the present embodiment, for image signals in the tolerance range of the subsequent circuit, the appropriate gain is searched by decreasing the gain of the controllable gain amplifier from the maximum value, step by step, until a saturated pixel appears, it can also be obtained by increasing the gain from a predetermined value, step by step, until all saturated pixels vanish. In this case, whether all saturated pixels have vanished is detected, so that the appropriate gain is obtained without the one-step back operation as is required in Step S109 and S310 in the first and second embodiments.

In the first embodiment, whether image signals of all the photodiodes of an imaging device are equal to the maximum level is confirmed so as to determine whether a saturated photodiode exists for image signals in the tolerance range; and in the second embodiment, whether image signals of all the pixels of an output device are equal to the median is confirmed so as to determine whether a saturated photodiode exists for image signals in the tolerance range. However, a predetermined permissible range or width about the maximum value or the median may be provided. For example, pixels or photodiodes of which values are within the permissible range or predetermined divisions around the maximum value or the median, are not determined as saturated pixels or saturated photodiodes, and only pixels or photodiodes of which the values are beyond the above permissible range are determined as saturated pixels or photodiodes. Further, the frequency (or the number of pixels) within the permissible range may be restricted.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2002-158462 (filed on May 31, 2002), which is expressly incorporated herein, by reference, in its entirety.

The invention claimed is:

1. An automatic gain control device for an electronic endoscope, comprising:
   a controllable gain amplifier that amplifies image signals output by an imaging device comprising a plurality of pixels;
   an A/D converter that digitizes the amplified image signals;
   a detector that detects a status of digitized amplified reference image signals output by the imaging device when the imaging device captures images of a white-balance test accessory; and
   a gain control processor that, based on the detected status of the digitized amplified reference image signals, sets a gain of the controllable gain amplifier to a value such that a linear operating range of an amplified image signal corresponding to a pixel of the plurality of pixels, having a smallest linear operating range out of the plurality of pixels, is approximately equal to a tolerance range of the A/D converter.

2. A device according to claim 1, wherein the detector comprises a histogram generator that generates a histogram based on the digitized amplified reference image signals.

3. A device according to claim 2, wherein said histogram indicates, for at least one image signal output value, a number of pixels corresponding to each of the at least one image signal output value.

4. A device according to claim 3, further comprising a saturated pixel detecting processor that determines whether a saturated pixel exists by determining whether a pixel corresponds to an image signal output value other than a predetermined image signal output value.

5. A device according to claim 1, wherein said reference image signals are luminance signals.

6. A device according to claim 5, wherein the value which the gain of the controllable gain amplifier is set to is a minimum gain value at which all of the digitized amplified reference image signals exceed a maximum value of the tolerance range of the A/D converter.

7. A device according to claim 1, wherein said reference image signals are color difference signals.

8. A device according to claim 7, wherein the value which the gain of the controllable gain amplifier is set to is a minimum gain value at which all of the digitized amplified reference image signals have a value corresponding to one-half a maximum value of the tolerance range of the A/D converter.

9. A device according to claim 1, wherein said gain control processor decreases said gain by a predetermined amount in successive steps, a saturated pixel detecting processor determines at each step whether a saturated pixel exists, and, when the saturated pixel detecting processor determines at a step that a saturated pixel exists, the gain control processor sets the gain to the gain of a previous step.

10. A device according to claim 1, wherein said gain control processor increases said gain by a predetermined amount in successive steps, a saturated pixel detecting processor determines at each step whether a saturated pixel exists, and, when the saturated pixel detecting processor determines at a step that a saturated pixel does not exist, the gain control processor maintains the gain at its present level.

11. A device according to claim 1, further comprising a memory that stores said gain, adjusted by said gain control processor.

12. A device according to claim 11, wherein said gain is stored in said memory together with information that is used to identify at least one electronic endoscope.

13. A device according to claim 11, further comprising
   a memory verification processor that determines whether said gain is stored in said memory; and
   a message indicating processor that indicates a message which prompts an execution of a gain control operation when said memory verification processor determines that said gain is not stored in said memory.

14. A device according to claim 1, wherein said gain control processor is driven when a white balance correction process is executed.

15. An electronic endoscope apparatus that comprises an automatic gain control device, the automatic gain control device comprising:
   a controllable gain amplifier that amplifies image signals output by an imaging device comprising a plurality of pixels;
   an A/D converter that digitizes the amplified image signals;
   a detector that detects a status of digitized amplified reference image signals output by the imaging device when the imaging device captures images of a white-balance test accessory; and a gain control processor that, based on the detected status of the digitized amplified reference image signals, sets a gain of the controllable gain amplifier to a value such that a linear operating range of an amplified image signal corresponding to a pixel of the plurality of pixels, having a smallest linear operating range out of the plurality of pixels, is approximately equal to a tolerance range of the A/D converter.

16. An apparatus according to claim 15, wherein a memory that stores information to identify an electronic endoscope is provided in said electronic endoscope apparatus.

17. An automatic gain control device for an electronic endoscope, comprising:
   a controllable gain amplifier that amplifies image signals output by an imaging device comprising a plurality of pixels;
   an image signal processor that processes the amplified image signals;
   a detector that detects a status of processed amplified reference image signals output by the imaging device when the imaging device captures images of a white-balance test accessory; and
   a gain control processor that, based on the detected status of the processed amplified reference image signals, sets a gain of the controllable gain amplifier to a value such that a linear operating range of an amplified image signal corresponding to a pixel of the plurality of pixels, having a smallest linear operating range out of the plurality of pixels, is approximately equal to a tolerance range of the image signal processor.

* * * * *